(12) United States Patent
Odermatt et al.

(10) Patent No.: US 9,101,515 B2
(45) Date of Patent: Aug. 11, 2015

(54) ABSORBENT MEDICAL BODY, IN PARTICULAR FOR REMOVING WOUND FLUIDS FROM HUMAN AND/OR ANIMAL BODY CAVITIES, AND METHOD FOR ITS PRODUCTION

(75) Inventors: Erich Odermatt, Schaffhausen (CH); Ingo Berndt, Tuttlingen (DE); Silke König, Rottweil (DE)

(73) Assignee: Aesculap AG (DE)

( * ) Notice: Subject to any disclaimer, the term of this patent is extended or adjusted under 35 U.S.C. 154(b) by 725 days.

(21) Appl. No.: 13/132,176

(22) PCT Filed: Dec. 3, 2009

(86) PCT No.: PCT/EP2009/008626
§ 371 (c)(1),
(2), (4) Date: Jun. 28, 2011

(87) PCT Pub. No.: WO2010/063467
PCT Pub. Date: Jun. 10, 2010

(65) Prior Publication Data
US 2011/0270205 A1 Nov. 3, 2011

(30) Foreign Application Priority Data
Dec. 3, 2008 (DE) .......... 10 2008 061 535

(51) Int. Cl.
| A61F 13/00 | (2006.01) |
| A61F 13/20 | (2006.01) |
| A61F 13/15 | (2006.01) |
| A61F 13/36 | (2006.01) |
| A61M 27/00 | (2006.01) |

(52) U.S. Cl.
CPC ........... *A61F 13/20* (2013.01); *A61F 13/15211* (2013.01); *A61F 13/36* (2013.01); *A61M 27/00* (2013.01); *A61F 2013/0054* (2013.01); *A61F 2013/00536* (2013.01); *A61F 2013/00642* (2013.01); *A61F 2013/15235* (2013.01)

(58) Field of Classification Search
CPC ........... A61F 13/15211; A61F 13/2054; A61F 13/2071; A61F 13/2088; A61F 2013/00642; A61F 2013/15219; A61F 2013/15227; A61F 2013/15235
USPC .......................... 604/304, 313–316, 364, 379
See application file for complete search history.

(56) References Cited

U.S. PATENT DOCUMENTS

| 2,057,206 A | * | 10/1936 | Pohl .............................. 604/377 |
| 3,805,785 A | * | 4/1974 | Marginet ........................ 604/12 |
| 4,034,759 A | * | 7/1977 | Haerr ............................ 604/514 |
| 4,098,728 A |   | 7/1978 | Rosenblatt |
| 4,317,447 A |   | 3/1982 | Williams |
| 5,578,662 A | * | 11/1996 | Bennett et al. .................. 524/54 |
| 5,678,564 A | * | 10/1997 | Lawrence et al. ............. 600/574 |
| 5,817,344 A |   | 10/1998 | Hoang et al. |
| 6,855,135 B2 | * | 2/2005 | Lockwood et al. ........... 604/313 |

(Continued)

FOREIGN PATENT DOCUMENTS

| DE | 26 57 684 A1 | 7/1977 |
| DE | 103 27 707 A1 | 4/2004 |
| DE | 699 32 612 T2 | 8/2007 |
| EP | 0 742 006 A1 | 11/1996 |

(Continued)

*Primary Examiner* — Lynne Anderson
(74) *Attorney, Agent, or Firm* — DLA Piper LLP (US)

(57) ABSTRACT

An absorbent medical body for removing wound fluids from human and/or animal body cavities includes a material which holds the absorbent body together in a compressed form and can be removed upon contact with a biocompatible liquid.

26 Claims, 1 Drawing Sheet

(56) References Cited

U.S. PATENT DOCUMENTS

| | | |
|---|---|---|
| 2002/0087136 A1 | 7/2002 | Widlund |
| 2006/0149170 A1* | 7/2006 | Boynton et al. .................. 601/6 |
| 2008/0103462 A1 | 5/2008 | Wenzel et al. |
| 2011/0014290 A1 | 1/2011 | Sing et al. |

FOREIGN PATENT DOCUMENTS

| | | |
|---|---|---|
| GB | 201834 A | 8/1923 |
| GB | 2 409 412 A | 6/2005 |
| RU | 2215508 | 11/2003 |
| WO | 2007/143060 A2 | 12/2007 |

* cited by examiner

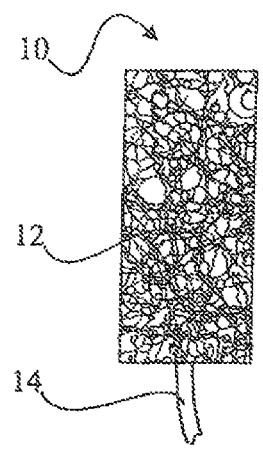
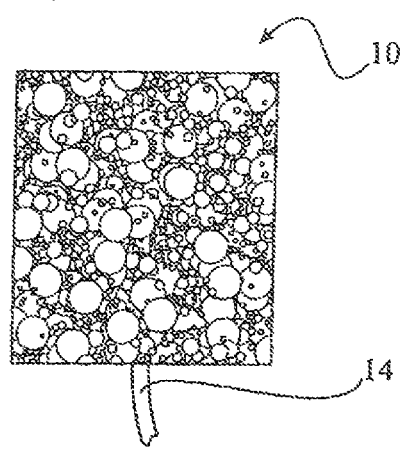
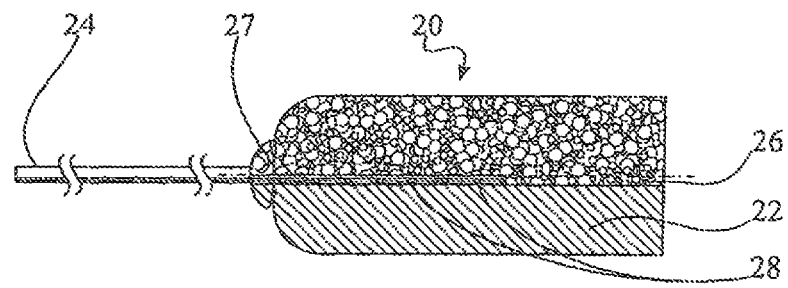
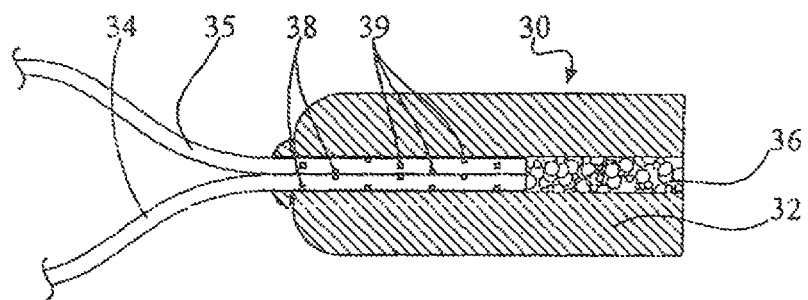

ABSORBENT MEDICAL BODY, IN PARTICULAR FOR REMOVING WOUND FLUIDS FROM HUMAN AND/OR ANIMAL BODY CAVITIES, AND METHOD FOR ITS PRODUCTION

RELATED APPLICATIONS

This is a §371 of International Application No. PCT/EP2009/008626, with an international filing date of Dec. 3, 2009 (WO 2010/063467 A1, published Jun. 10, 2010), which is based on German Patent Application No. 102008061535.8, filed Dec. 3, 2008, the subject matter of which is incorporated by reference.

TECHNICAL FIELD

This disclosure relates to an absorbent medical body which is suitable primarily for removing wound fluids from human and/or animal body cavities, and to a production method for the absorbent body.

BACKGROUND

One possible way of treating infectious body cavities is provided by so-called "endoluminal vacuum therapy." This form of therapy employs a special wound drainage system which is composed essentially of an open-pore sponge for absorbing wound secretions and a drainage tube for removing or discharging the absorbed wound secretions. Such a wound drainage system is marketed by B. Braun Aesculap AG under the name "Endo-SPONGE."

In general, the sponge is placed in the relevant body cavity with an applicator system consisting of a tube- or pipe-like overtube and a pusher, by which the sponge is pushed through the overtube. The sponge is folded or pressed together, or compressed, by the overtube. After emerging from the overtube, the sponge unfolds again immediately and in this state is ready to absorb wound secretions. A disadvantage of this is that once it has unfolded, the sponge can generally no longer be repositioned or re-placed inside the body cavity. Since even with a preliminary endoscopic study of the relevant body cavity, there is not always a guarantee that the sponge can be brought into the desired position inside the body cavity at the first attempt, a repositionably designed sponge would be of great medical benefit.

It could therefore be helpful to provide an absorbent medical body which can be positioned in a body cavity without using an overtube and, above all, can optionally be repositioned several times inside the body cavity.

SUMMARY

We provide an absorbent medical body for removing wound fluids from human and/or animal body cavities including a material which holds the absorbent body together in a compressed form and can be removed upon contact with a biocompatible liquid.

We also provide a method for producing the absorbent medical body including compressing an absorbent body into a compressed form, wetting or soaking the absorbent body provided in the compressed form with a solution or suspension including a material which is removable upon contact with a biocompatible liquid and a solvent or solvent mixture, and drying the compressed and wetted or soaked absorbent body by removing the solvent or solvent mixture.

BRIEF DESCRIPTION OF THE DRAWINGS

FIG. 1a shows side view of an absorbent medical body.
FIG. 1b shows side view of the absorbent body represented in FIG. 1a, after removing the material which has held the absorbent body together in a compressed form.
FIG. 2 shows another example of an absorbent medical body.
FIG. 3 shows another example of an absorbent medical body.

DETAILED DESCRIPTION

The absorbent body is an absorbent medical body, in particular for removing wound fluids from human and/or animal body cavities, comprising a material which holds the absorbent body together in a compressed form and can be removed or is removable upon contact with a biocompatible liquid.

We provide an absorbent medical body which, owing to a material that can be removed upon contact with a biocompatible liquid, preferably a biocompatible flushing or rinsing liquid, is provided in a compact form or is held in such a form. Upon contact with wound fluids, however, the material is not removed or is removed only with a long delay so that the absorbent body does not unfold after placement in an infectious wound cavity, or unfolds only with a long delay. In other words, contact of the absorbent body with wound fluids does not initiate uncontrolled unfolding or expansion of the absorbent body. This may be used particularly advantageously for repositioning, and sometimes also for repeated repositioning, of the absorbent body inside the body cavity. Once the absorbent body has been optimally positioned inside the body cavity in terms of therapy, the unfolding or expansion of the absorbent body may be accelerated by flushing the absorbent body with a biocompatible or physiologically compatible liquid. It is therefore no longer necessary to use an overtube or the like.

The terms "absorbent medical body" and "absorbent body" are used interchangeably.

As already mentioned, the absorbent body is suitable for removing wound fluids or wound secretions, i.e., pathological fluid accumulations, from human and/or animal body cavities. To this end, the absorbent body is preferably used in the scope of endoluminal vacuum therapy which will be described in more detail below. The absorbent body may, for example, be used for treating abscesses, in particular intra-abdominal or intracavity abscesses, fistulas, inflammation of the pancreas or the like. In the case of fistulas, the absorbent body may be in particular used for the treatment of fistulas of the small intestine and/or gall bladder.

The body cavities are generally so-called "wound cavities." This is intended to mean naturally occurring or pathologically induced protuberances, generally of hollow organs, like blood vessels, the large intestine, small intestine, gall bladder, esophagus, urethra and the like. For example, the protuberances may be present as diverticels, aneurysms, fistulas and/or abscesses in the body of a patient. The aforementioned protuberances may become filled with wound secretions. Pathologically induced protuberances are often the result of operational interventions, in particular anastomotic insufficiencies. Protuberances may be formed in the ligature or suture region, and may rapidly become larger owing to an infection. Protuberances in the region of the suturing are often also referred to as so-called "insufficiency cavities."

The wound fluids are pathological fluids, in particular wound secretions, exudates, abscess fluids or intestinal contents. Suitable biocompatible liquids for removing the material, which holds the absorbent body together in a compressed form, may in principle be all physiologically compatible liquids, in particular buffer or electrolyte solutions, for example, 0.9% strength sodium chloride solution, water or Ringer (lactate) solution.

Preferably, the material can be removed or is removable upon contact with a biocompatible liquid, preferably a biocompatible flushing liquid, within a time of <60 seconds, in particular from 2 to 30 seconds, preferably from 2 to 15 seconds. The material can particularly preferably be dissolved or is preferably dissolvable upon contact with a biocompatible liquid.

The material may at least partially, and preferably completely, penetrate the absorbent body. For instance, the material may be formed in the absorbent body over a depth of between 1 and 99%, in particular 10 and 50%, expressed in terms of the diameter of the absorbent body. The proportion of the material is preferably between 0.1 and 30 wt. %, in particular 0.3 and 30 wt. %, preferably 1 and 15 wt. %, expressed in terms of the total weight of the absorbent body.

Preferably, the material is formed as a three-dimensional network which preferably interpenetrates the absorbent body.

The material may furthermore be formed in the manner of a coating, preferably a partial coating, on and/or inside the absorbent body. For example, the material may essentially be formed only on the absorbent body surface. In particular, the material may essentially be formed only, and preferably exclusively, on the surface of the absorbent body. The material may furthermore be formed at least partially continuously, in particular at least partially covering, on the surface of the absorbent body.

Substructures, especially pore webs, of the absorbent body may at least partially, and in particular partially, encapsulated or coated by the material. In particular, openings, preferably pores, of the absorbent body are at least partially, and in particular partially, covered by the material.

Preferably, the material is provided in a dried, preferably freeze-dried, form. The material is preferably selected from the group consisting of proteins, polysaccharides, in particular cellulose derivatives and/or mucopolysaccharides and polymers, in particular from the group consisting of collagen, elastin, gelatine, dextran, methyl cellulose, hydroxymethyl cellulose, hydroxyethyl cellulose, hydroxypropyl cellulose, carboxymethyl cellulose, dextran, hyaluronic acid, chondroitin sulfate, alginic acid, chitosan, heparin, polyvinyl alcohol, polyethylene glycol and mixtures thereof.

Alternatively, the material is a low molecular weight compound and/or a salt.

Preferably, the absorbent body in the compressed form has a volume reduced by from 10 to 90%, in particular from 20 to 80%, preferably from 40 to 70%, expressed in terms of the volume of the absorbent body without the material (original volume of the absorbent body). The absorbent body in the compressed form is preferably formed so that it is flexible, in particular bendable. In other words, the absorbent body preferably has no brittleness.

The absorbent body in the compressed form may furthermore be formed so that it is extensible, in particular elastically. This offers certain advantages in respect of handling the absorbent body, in particular when it is being placed in a body cavity.

Generally, the absorbent body may be designed as a pad, membrane, sponge or foam body. Preferably, the absorbent body is formed as a sponge or foam body, preferably a sponge body. A sponge body particularly advantageously has a larger absorbent surface area.

The compressed absorbent body may furthermore in principle be provided in various shapes. For instance, starting from a basic shape, the absorbent body may be adapted in shape and size, in particular cut, for a body cavity to be treated. For example, the absorbent body may have a circular, oval, triangular, square, trapezoidal, rhomboid, pentagonal or five-sided, hexagonal, star- or cross-shaped cross section. The absorbent body may also be formed as a hollow body, for example, as a tube, pipe or hollow cylinder.

The absorbent body is furthermore preferably provided compressed in two dimensions. For example, the absorbent body may be provided in a radially compressed form.

The absorbent body itself may preferably be a sponge or foam body, preferably a sponge body. The absorbent body itself is generally formed from a polymer. The polymer may be a homo- or copolymer. A copolymer is intended to mean a di-, tri-, tetrapolymer or the like. In other words, the term "copolymer" preferably means a polymer that comprises two or more different monomer units. The absorbent body is preferably formed from a non-absorbable polymer, in particular selected from the group consisting of polypropylene, polyethylene, polyethylene terephthalate, polyurethane, silicone, polyvinyl alcohol, copolymers thereof and mixtures, in particular blends, thereof. The absorbent body is in particular formed from polyurethane or a polyurethane derivative, in particular polyurethane ether or polyurethane ester. The polyurethane may be an aliphatic polyurethane. The polyurethane is preferably a linear aliphatic polyurethane. The polyurethane itself may be formed from macromolecular and/or low molecular weight aliphatic diols and aliphatic diisocyanates. Primarily polycarbonates, in particular 1,6-hexanediol polycarbonate, may be envisaged as macromolecular diols. For example, 2,2,4-trimethylhexanediol, 2,4,4-trimethylhexanediol, and/or 1,4-butanediol may be used as low molecular weight diols. Preferably cycloaliphatic diisocyanates, in particular 4,4-dicyclohexylmethane diisocyanate or 1,4-cyclohexyl diisocyanate, may be envisaged as aliphatic diisocyanates. The polyurethane may furthermore be produced from different diols and/or diisocyanates. Polyurethane is particularly preferred as a material for the absorbent body owing to its biocompatibility.

Alternatively, the absorbent body is formed from an absorbable polymer. For example, the polymer may be selected so that it has an absorption time of between 60 and 120 days. Suitable polymers are, for example, selected from the group consisting of polylactide, polyglycolide, poly-ε-caprolactone, trimethylene carbonate, poly-para-dioxanone, hydroxybutyric acid, copolymers thereof and mixtures, in particular blends, thereof. Further, the absorbent body may be formed from a co- or terpolymer, in particular a block co- or block terpolymer, comprising at least one monomer selected from the group consisting of lactide, glycolide, ε-caprolactone, trimethylene carbonate, para-dioxanone and hydroxybutyric acid, copolymers thereof and mixtures, in particular blends, thereof.

The absorbent body is preferably formed so that it is open-porous or open-pored. The absorbent body may in principle have a pore size of between 100 and 1500 μm, in particular 200 and 1000 μm, preferably 400 and 800 μm, more preferably 400 and 600 μm. If the absorbent body is formed, for example, from polyurethane, then the pore size preferably lies in the range of between 400 and 600 μm. On the other hand, the pore size of an absorbent body made of polyvinyl alcohol may lie between 200 and 1000 μm.

The absorbent body and/or the material which holds the absorbent body together in a compressed form may comprise active agents, in particular selected from the group consisting of antimicrobial, antiseptic, disinfectant, growth-promoting, odor-inhibiting and/or anti-inflammatory active agents. For example triclosan, polyhexamethylene biguanide (PHMB), copper, zinc, silver, compounds thereof and salts thereof may be mentioned as antimicrobial active agents. The active agents may generally be provided in particulate form, particularly in the form of nano- and/or microparticles.

In another preferred embodiment preferably, the absorbent body comprises a gel, a paste or a lubricant cream. The gel or the paste, or the lubricant cream, preferably have hydrophilic properties and particularly advantageously prevent uncontrolled deployment of the absorbent body. In general, the absorbent body is provided with a corresponding gel or a corresponding paste or lubricant cream before it is placed in an infectious body cavity. The gel or the paste, or the lubricant cream, is usually applied onto the surface of the absorbent body and therefore prevents the absorbent body from being deployed uncontrollably. Once the absorbent body has been placed optimally in the body cavity, the gel is preferably flushed away together with the material which can be removed upon contact with a biocompatible liquid.

Preferably, the absorbent medical body comprises a drainage tube. The drainage tube may particularly advantageously fulfill two functions. On the one hand, the drainage tube is used for preferably continuous removal or discharge of liquid quantities absorbed by the absorbent body. On the other hand, after it has been placed in a body cavity, the absorbent body may also be deliberately flushed through the drainage tube, for example, with water or an aqueous solution, so that the material which holds the absorbent body together in a compressed foam can advantageously be removed more rapidly, in particular dissolved. This in turn leads to more rapid unfolding of the absorbent body inside the body cavity.

The absorbent body is preferably connected integrally to a drainage tube. In the case of the drainage tube, distinction can generally be made between a proximal (near the body) and a distal (away from the body) tube end. The drainage tube is preferably connected to the absorbent body with its proximal end, whereas the distal end of the drainage tube is free. The distal end may, for example, be connected in the scope of endoluminal vacuum therapy to a suction or vacuum source, in particular a suction or vacuum pump. With the aid of a suction or vacuum source, a negative pressure or suction of between 400 and 900 mbar, in particular 500 and 800 mbar, may be generated. Particularly rapid cleaning of infectious body cavities is therefore possible. The vacuum source may be a portable vacuum source, in particular a portable vacuum pump or vacuum bottle. In this way, the patient's mobility can be maintained during the treatment.

In principle, the absorbent body may be provided for placement in a body cavity for several hours to several days. The absorbent body is typically changed every 8 to 72 hours. The quantities of fluid removed or discharged are normally gathered in collection containers intended for this, for example, canisters or vacuum bottles. The collection containers are generally connected upstream of a suction or vacuum source and are in contact with it through suitable connection tubes. To avoid contaminating a suction or vacuum source, a sterile filter may be provided between the collection containers and a suction or vacuum source. The absorbent body may furthermore be formed integrally on a drainage tube. For example, the absorbent body may be adhesively bonded, stitched or welded to a drainage tube and/or expansion-molded onto a drainage tube. The absorbent body and the drainage tube may also be formed so that they can be fitted together. In particular, the absorbent body and drainage tube may be formed so that the drainage tube can be integrated into the absorbent body material. In general, at least a part of the drainage tube will be enclosed or encapsulated by the absorbent body. For example, to this end the absorbent body has an essentially cylindrically shaped through-channel which is preferably formed extending in the longitudinal direction of the absorbent body. The through-channel may furthermore be formed by cross- or star-shaped stamping (without material being removed). The through-channel usually extends centrally through the absorbent body. Expediently, the through-channel has a diameter which is adapted to the diameter of the drainage tube. That part of the drainage tube which is encapsulated by the absorbent body conventionally has openings. A uniform negative pressure can therefore particularly advantageously be generated on the entire absorbent body. The openings also permit more rapid and more efficient discharge of the wound fluids absorbed by the absorbent body.

The drainage tube itself is preferably formed from a liquid-impermeable, in particular air-impermeable material, in particular a polymer. For example, the drainage tube may be a plastic or synthetic tube. Suitable materials for the drainage tube are, for example, polyethylene, polypropylene, polyvinyl chloride or polyurethane.

The absorbent body may comprise a drainage tube which is a liquid-tightly encapsulated section, in particular a tubular projection, of the absorbent body. The encapsulation may be formed as a film, in particular an adhesive film. For example, the encapsulation may be formed from a hot-melt adhesive. Both absorbable and non-absorbable materials may be envisaged as a hot-melt adhesive. Absorbable hot-melt adhesives may, for example, be selected from the group consisting of polyglycolides, polylactides, polydioxanones, polycaprolactones and copolymers thereof. Polymer blends may also be envisaged.

The absorbent body may comprise a flushing or rinsing tube. The absorbent body preferably comprises both a drainage tube and a flushing tube. The flushing tube is preferably used for deliberate flushing of the absorbent body to remove more rapidly the material which holds the absorbent body together in a compressed form. The flushing or rinsing liquid used may, for example, be a sodium chloride solution, buffer solution, anti-inflammatory, odor-inhibiting and/or antimicrobial solution. With respect to other features and details of the flushing tube, reference is made to the structures described for the drainage tube.

As already mentioned, the absorbent medical body is preferably used for draining body cavities with pathological liquid accumulations, i.e., infectious body cavities. It is therefore particularly preferable for the absorbent medical body to be provided as a drainage article or drainage product for removing or discharging pathological liquid accumulations from human and/or animal body cavities.

We also provide a method for producing the absorbent medical body, comprising the following steps:
  a) putting an absorbent body into a compressed form,
  b) wetting or soaking the absorbent body, provided in the compressed form, with a solution or suspension comprising a material which can be removed or is removable upon contact with a biocompatible liquid and a solvent or solvent mixture,
  c) drying the compressed and wetted or soaked absorbent body by removing the solvent or solvent mixture.

Preferably, the absorbent body is put into the compressed form by putting it into a hollow body, in particular a sleeve, a tube or a pipe. The hollow body is preferably a small pipe, for example, an aluminium or stainless steel pipe. For wetting or soaking with the solution or suspension, one end of the hollow body may be closed with a plug suitable for this so that the wetting or soaking of the absorbent body provided in a compressed form with the solution or suspension takes place through a still open other end of the hollow body. The absorbent body may be removed from the hollow body already before the drying step or not until after it. If the absorbent body is removed from the hollow body before drying, it may be advantageous for the hollow body and the absorbent body to be subjected to a freezing process beforehand.

To wet or soak the absorbent body, it is preferably immersed into the solution or suspension. As an alternative to this, the absorbent body may also be sprayed with the solution or suspension. Furthermore, a solution or suspension may be used which has a proportion of the material between 0.1 and 30 wt. %, in particular 0.3 and 30 wt. %, preferably 1 and 15 wt. %, expressed in terms of the total weight of the solution or suspension.

It is furthermore preferable for a negative pressure or vacuum to be generated on the absorbent body during or after the wetting or soaking of the absorbent body, so that the solution or suspension penetrates fully through the absorbent body. To this end, in principle a drainage or flushing tube, which is preferably connected in one piece or integrally to the absorbent body, may be connected to a negative pressure or vacuum source. Preferably, however, the compressed and wetted or soaked absorbent body is placed in a vacuum cabinet.

Preferably, the absorbent body is dried by freeze-drying or lyophilization. As an alternative, the absorbent body may also be dried by applying heat, in particular at a temperature of between 60 and 130° C. For example, the absorbent body may be dried in a heating cabinet. The drying removes the solvent or solvent mixture and dries the material which is intended to hold the absorbent body together in the compressed form. By the dried material, the absorbent body is held in a compressed form or in a compressed state.

With respect to other features and details of the method, reference is made to the description above.

Lastly, we provide for the use of an absorbent body and a material which can be removed or is removable upon contact with a biocompatible liquid for producing an absorbent medical body, in particular for removing wound fluids from human and/or animal body cavities. With respect to other features and details, particularly in relation to the absorbent body and the material which can be removed upon contact with a biocompatible liquid, full reference is made to the description above.

Other features and details of the invention may be found in the following description of preferred structures in the form of figure descriptions and an example. The figures are hereby made part of the content of this description by explicit reference. The individual features may respectively be implemented on their own, or several together in combination with one another. The figures, including the associated figure descriptions, and the example merely serve to explain the body and method without in any way restricting it thereto.

Turning now to the drawings, FIG. 1a shows the side view of an absorbent body 10. The absorbent body 10 comprises a material 12 which holds the absorbent body 10 together in a compressed form and can be removed upon contact with a biocompatible liquid. In this form, the absorbent body 10 can particularly advantageously be placed in a body cavity without using an overtube and, if necessary, can also be re-placed inside the body cavity. Optionally, the compressed absorbent body 10 may be re-placed several times in succession until the absorbent body 10 occupies an optimal position inside the body cavity. The material itself may, for example, be a protein, polysaccharide or a synthetic polymer or a low molecular weight compound, for example, a salt or a sugar. The wound fluid absorbed by the absorbent body 10 can be discharged through the drainage tube 14.

Once the absorbent body 10 has been positioned optimally inside the body cavity in terms of therapy, the material 12 may be removed from the absorbent body 10 by deliberate flushing with a biocompatible liquid, so as to accelerate the spreading or expansion of the absorbent body 10, provided in a compressed form, inside the body cavity. The time taken for complete removal of the material 12 may be deliberately adjusted via the concentration of the solution or suspension which is used for wetting or soaking the absorbent body 10 provided in the compressed form.

FIG. 2 shows an absorbent body 20. It is shaped cylindrically or tubularly and comprises a drainage tube 24. After it has been placed in a body cavity, the absorbent body can be flushed deliberately through the drainage tube 24, for example, with a suitable buffer solution, so as to remove the material 22 (represented by shading) which holds the absorbent body 20 together in a compressed form. The material 22 can be removed particularly rapidly by flushing the absorbent body 20 through the drainage tube 24, generally within a time of less than one minute. The absorbent body 20 has a cylindrically shaped through-channel 26, which extends approximately centrally in its longitudinal direction and into which the drainage tube 24 partially projects. To fasten the absorbent body 20 on the drainage tube 24, the absorbent body 20 is additionally knotted to the drainage tube 24 by a thread 27. With the aid of the drainage tube 24, the wound fluids absorbed from infectious body cavities by the absorbent body 20 can also be removed or discharged. This may, for example, be done by applying a negative pressure or vacuum to the free (distal) end of the drainage tube 24. In general, for this purpose the drainage tube 24 is connected to a suction pump. The drainage tube 24 additionally comprises openings 28 in its wall. These make it possible to apply a uniform negative pressure or vacuum to the absorbent body 20, and thereby contribute to rapid removal or discharge of the wound fluids from the relevant body cavities.

FIG. 3 shows an absorbent body 30, which comprises a drainage tube 34 and a flushing tube 35. The absorbent body 30 is held together in a compressed formed by a material 32 (represented by shading). The tubes 34 and 35 project together into a cylindrical through-channel 36 of the absorbent body 30. The tubes 34 and 35 also comprise openings 38 and 39, respectively. The through-channel 36 extends approximately centrally through the absorbent body 30 in its longitudinal direction. In this example, the flushing tube 35 is used for deliberate flushing of the absorbent body 30 to remove the material 32. Owing to the resultant unfolding of the absorbent body 30, it is capable of absorbing amounts of liquid which have built up in body cavities. The absorbed wound fluids can then be discharged through the drainage tube 34. With respect to other features, reference is made to the description for FIG. 2.

EXAMPLE

Production of an Absorbent Body

First, 15 g of polyvinyl alcohol granules and 985 g of fully deionized water were placed in 1 l Schott flasks. To accelerate dissolving of the polyvinyl alcohol, the flasks were subsequently placed overnight at 95° C. in a heating cabinet. After the polyvinyl alcohol had fully dissolved, the Schott flasks were removed again from the heating cabinet so that the resulting polyvinyl alcohol solutions (PVA solutions) could be heated to room temperature.

Polyurethane sponges with an average pore size of about 600 μm, each of which was integrally connected to a drainage tube, were used as absorbent bodies. Initially, the sponges were respectively pulled into small stainless steel pipes. The following procedure was adopted for each sponge. First, in each case, a suitable insertion aid was put onto the stainless steel pipes and the sponge was pulled through. The insertion aids were then removed again and, if appropriate, the sponges were re-placed slightly until the sponge ends respectively were entirely in the pipes. Next, one end of the pipes was respectively closed with a plastic plug. The drainage tube protruded from each unclosed end of the stainless steel pipes. To prevent polyvinyl alcohol solution from entering the drainage tubes in the step described below, they were clamped off by means of a tube clip.

The pipes were then placed in a rack with holes, the drainage tubes protruding from the pipes being temporarily bound together to facilitate further handling. The hole rack with the stainless steel pipes inserted in it was subsequently placed in a trough provided for this purpose. The trough was then filled with one of the PVA solutions described above, the filling level lying about 2 cm above the open ends of the pipes. This ensured that the cavity enclosed by the pipes could be filled optimally with the polyvinyl alcohol solution and the liquid level did not sink below the open ends of the pipes. The trough filled in this way was subsequently placed in a vacuum chamber. A vacuum was then applied a total of three times in succession. In this way, it was possible to ensure that the pipes were completely filled and there were no longer any small air inclusions in them. After the vacuum treatment, the hole rack was removed again from the trough. Excess polyvinyl alcohol solution was allowed to drip from the surfaces of the pipes and the hole rack.

For pre-freezing, either the complete rack was placed in a freezing cabinet or the pipes were first removed from the hole rack and fastened individually in a freezing cabinet with clips. The pipes with the polyurethane sponges contained in them usually remained in the freezing cabinet for at least 5 to 6 hours. After pre-freezing, the tube clips and the plastic plugs were removed and the frozen polyurethane sponges were pulled out of the pipes. The frozen polyurethane sponges were subsequently placed in green PTFE cups and put into a lyophilizer for one night for freeze-drying. It is recommendable that the lyophilizer should already be pre-frozen. After the lyophilization, the sponges were vacuum-packed individually in white aluminium bags. The packaging was carried out by means of a Multivac packaging machine. The sponges packed in this way were then subjected to γ-sterilization.

The invention claimed is:

1. An absorbent medical body that removes wound fluids from human and/or animal body cavities comprising a material which holds the absorbent body together in a compressed form and can be removed upon contact with a biocompatible liquid, wherein the material is a three-dimensional network interpenetrating the absorbent body and is formed as a partial coating on and/or inside the absorbent body and openings in the absorbent body are partially covered by the material.

2. The absorbent medical body according to claim 1, wherein the material dissolves upon contact with a biocompatible liquid.

3. The absorbent medical body according to claim 1, wherein the material is formed as a partial coating, on and/or inside the absorbent body.

4. The absorbent medical body according to claim 1, wherein the openings are pore webs partially encapsulated by the material.

5. The absorbent medical body according to claim 1, wherein the openings are pores partially covered with the material.

6. The absorbent medical body according to claim 1, wherein a proportion of the material is between 0.3 and 30 wt. % expressed in terms of the total weight of the absorbent body.

7. The absorbent medical body according to claim 1, wherein the material is in a freeze-dried form.

8. The absorbent medical body according to claim 1, wherein the material is selected from the group consisting of proteins, polysaccharides, cellulose derivatives and/or mucopolysaccharides, and polymers, collagen, elastin, gelatine, dextran, methyl cellulose, hydroxymethyl cellulose, hydroxyethyl cellulose, hydroxypropyl cellulose, carboxymethyl cellulose, dextran, hyaluronic acid, chondroitin sulfate, alginic acid, chitosan, heparin, polyvinyl alcohol, polyethylene glycol and mixtures thereof.

9. The absorbent medical body according to claim 1, wherein the material is a low molecular weight compound and/or a salt.

10. The absorbent medical body according to claim 1, wherein the absorbent body in the compressed form has a volume reduced by from 10 to 90% expressed in terms of the volume of the absorbent body without the material.

11. The absorbent medical body according to claim 1, wherein the absorbent body in the compressed form is formed so that it is flexible.

12. The absorbent medical body according to claim 1, wherein the absorbent body in the compressed form is formed so that it is elastic.

13. The absorbent medical body according to claim 1, wherein the absorbent body is a sponge or foam body.

14. The absorbent medical body according to claim 1, wherein the absorbent body is formed from a non-absorbable polymer selected from the group consisting of polypropylene, polyethylene, polyethylene terephthalate, polyurethane, silicone, polyvinyl alcohol, derivatives thereof, copolymers thereof and mixtures thereof.

15. The absorbent medical body according to claim 1, wherein the absorbent body is formed from an absorbable polymer selected from the group consisting of polylactide, polyglycolide, poly-ϵ-caprolactone, trimethylene carbonate, poly-para-dioxanone, hydroxybutyric acid, copolymers thereof and mixtures thereof.

16. The absorbent medical body according to claim 1, wherein the absorbent body is formed from a co- or terpolymer, comprising at least one monomer selected from the group consisting of lactide, glycolide, ϵ-caprolactone, trimethylene carbonate, para-dioxanone and hydroxybutyric acid.

17. The absorbent medical body according to claim 1, wherein the absorbent body comprises pores with a diameter of between 100 and 1500 μm.

18. The absorbent medical body according to claim 1, wherein the absorbent body comprises a drainage tube and, optionally, a flushing tube.

19. The absorbent medical body according to claim 1, wherein the absorbent body is a drainage article for discharging pathological fluid accumulations from human and/or animal body cavities.

20. A method for producing an absorbent medical body according to claim 1, comprising:
  a) compressing an absorbent body into a compressed form,
  b) wetting or soaking the absorbent body provided in the compressed form with a solution or suspension comprising a material which is removable upon contact with a biocompatible liquid and a solvent or solvent mixture, c) drying the compressed and wetted or soaked absorbent body by removing the solvent or solvent mixture.

21. The method according to claim 20, wherein the absorbent body is compressed by insertion into a hollow body.

22. The method according to claim 20, wherein, to wet or soak the absorbent body, the absorbent body is immersed in the compressed form into the solution or suspension.

23. The method according to claim 20, wherein, to wet or soak the absorbent body, the absorbent body is sprayed in the compressed form with the solution or suspension.

24. The method according to claim 20, wherein a solution or suspension has a proportion of the material between 0.3 and 30 wt. %, expressed in terms of the total weight of the solution or suspension.

25. The method according to claim 20, wherein, during or after the wetting or soaking of the absorbent body, a negative pressure or vacuum is generated so that the solution or suspension penetrates fully through the absorbent body.

26. The method according to claim 20, wherein the absorbent body is dried by lyophilization.

* * * * *